US00PP23769P3

(12) United States Plant Patent
Lommerse

(10) Patent No.: US PP23,769 P3
(45) Date of Patent: Jul. 23, 2013

(54) ***DAHLIA* PLANT NAMED 'LOMDAHBRS'**

(50) Latin Name: ***Dahlia* hybrid**
Varietal Denomination: LOMDAHBRS

(75) Inventor: Henry Lommerse, Mariahout (NL)

(73) Assignee: Lommerse Holding BV (NL)

( * ) Notice: Subject to any disclaimer, the term of this patent is extended or adjusted under 35 U.S.C. 154(b) by 421 days.

(21) Appl. No.: 12/924,599

(22) Filed: Sep. 30, 2010

(65) Prior Publication Data

US 2012/0084894 P1 Apr. 5, 2012

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — Cassandra Bright

(57) ABSTRACT

A new and distinct *Dahlia* cultivar named 'LOMDAHBRS' is disclosed, characterized by distinctive strong red flowers, a compact plant with a floriferous habit, and free branching. The new variety is a *Dahlia,* normally produced as an outdoor ornamental plant for containers or gardens.

1 Drawing Sheet

Latin name of the genus and species: *Dahlia* hybrid.
Variety denomination: 'LOMDAHBRS'.

BACKGROUND OF THE INVENTION

The new cultivar was discovered as a result of a planned breeding program directed by the inventor, Henry Lommerse a citizen of the Netherlands. The parent is an undistributed, unpatented proprietary variety *Dahlia* hybrid '25079' and the pollen parent is the undistributed, unpatented proprietary variety *Dahlia* hybrid '25075.' The new variety was discovered as a seedling in June 2006, by the inventor in a commercial research greenhouse in Mariahout, the Netherlands.

Asexual reproduction of the new cultivar 'LOMDAHBRS' by vegetative cuttings was first performed in 2008, at a research greenhouse in Mariahout, the Netherlands. Multiple generations have since been produced and have shown that the unique features of this cultivar are stable and reproduced true to type in successive generations.

SUMMARY OF THE INVENTION

The cultivar 'LOMDAHBRS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOMDAHBRS' These characteristics in combination distinguish 'LOMDAHBRS' as a new and distinct *Dahlia* cultivar:

1. Sturdy plant with a compact habit
2. Strong red flower color
3. Good branching characteristics
4. Floriferous habit.

PARENT COMPARISON

Plants of the new cultivar 'LOMDAHBRS' are similar to plants of the seed parent, *Dahlia* hybrid '25079' in most horticultural characteristics, however, plants of the new cultivar 'LOMDAHBRS' produce more flowers, bloom for a longer period of time and produce more ray florets than '25079'. Additionally, plants of the parent variety are less sturdy and more open then 'LOMDAHBRS.'

Plants of the new cultivar 'LOMDAHBRS' are similar to plants of the pollen parent, *Dahlia* hybrid '25075' in most horticultural characteristics, however, plants of the new cultivar 'LOMDAHBRS' produce more flowers with a brighter red color, and foliage that is more resistant to damage.

COMMERCIAL COMPARISON

'LOMDAHBRS' can be compared to the commercial variety *Dahlia hybrida* 'Singer' U.S. Plant Pat. No. 11,315. The two varieties are similar in many horticultural characteristics, including having a similar flower color. However, plants of 'LOMDAHBRS' differ in producing more branches, and a more compact plant shape than 'Singer.' Additionally plants of 'LOMDAHBRS' begin flowering earlier from a rooted cutting than 'Singer.' Flower form is also different between the two varieties, with 'LOMDAHBRS' producing a more spherical, less flattened flower form.

The new variety can also be compared to the commercial variety unpatented *Dahlia variabilis,* 'Dapared'. U.S. Plant Pat. No. 17,143. *Dahlia* 'LOMDAHBRS' and *Dahlia* 'Dapared' are similar in many horticultural characteristics, including a similar flower color. However, plants of 'LOMDAHBRS' are more vigorous, produce more flowers and branches per plant, and larger flowers than 'Dapared.'

BRIEF DESCRIPTION OF THE PHOTOGRAPH

The accompanying photograph in FIG. 1 illustrates in full color a typical plant of 'LOMDAHBRS' grown in a outdoors, in Mariahout, the Netherlands, in a commercial 20 cm container.

Age of the plant photographed is approximately 70 days from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'LOMDAHBRS' plants grown outdoors, in the ground during the Summer months in Mariahout, the Netherlands. The growing temperature ranged from 16° C. to 27° C. daytime and 16° to 18° C. at night. One treatment of the growth regulator daminozide 85% at a rate of approximately 0.1%, was applied at approximately 2 weeks after planting the rooted cutting. Measurements and numerical values represent averages of typical plant types.

Botanical classification: *Dahlia* hybrid 'LOMDAHBRS.'

PROPAGATION

Time to initiate roots:

*Summer.*—13-15 days days at approximately 20-18 (day-night) ° C.

*Winter.*—19-23 days at approximately 18-16 (day-night) ° C.

Root description: Fibrous.

Tuber description:

*Average length.*—10.5 cm, average thickness: 1.1 cm, Coloured near RHS Greyed-Yellow 161D.

Propagation method: Vegetative cuttings.

PLANT

Age of plant described: 70 days from a rooted cutting.

Growth habit: Broad inverted triangular, broad upright.

Pot size of plant described: Field grown.

Height: Approximately 39.6 cm.

Plant spread: Approximately 57.4 cm.

Growth rate: Low to moderate.

Branching characteristics: Very free branching.

Length of primary lateral branches: Average 22.7 cm.

Quantity of primary lateral branches: Approximately 27.

Characteristics of primary lateral branches:

*Diameter.*—Approximately 0.7 cm.

*Color.*—Near RHS Yellow-Green 144A.

*Texture.*—Smooth.

*Strength.*—Moderately strong.

Internode length: Average 5.1 cm.

FOLIAGE

Leaf:

*Arrangement.*—Compound, with 3 or 5 leaflets per leaf.

*Shape.*—Overall shape ovate.

*Quantity.*—Approximately 8 per branch (4 pairs).

*Average overall length.*—11.4 cm.

*Average overall width.*—10.4 cm.

Individual leaflet blades:

*Shape of blade.*—Ovate to elliptic.

*Apex.*—Apiculate.

*Base.*—Acuminate.

*Margin.*—Serrate.

*Texture of top surface.*—Smooth.

*Pubescence.*—No leaf pubescence on upper side; veins on under side and margins sparsely pubescent, average length of hairs: 0.2 mm, coloured green-white, too small for the colour to be accurately measured with R.H.S.-Colour Chart.

*Aspect.*—Leaves placed in an average angle of 40° to lateral branch.

*Color.*—Young foliage upper side: Near RHS Green N137C. Young foliage under side: Near RHS Yellow-Green 147B. Mature foliage upper side: Near RHS Yellow-Green 147A. Mature foliage under side: Near RHS Yellow-Green 148B.

*Venation.*—Type: Pinnate. Venation color upper side: Near RHS Yellow-Green 147B. Venation color under side: Near RHS Yellow-Green 147B.

*Petiole.*—Length: Approximately 3.5 cm. Diameter: Approximately 0.25 cm. Color: Near RHS Yellow-Green 144A. Texture: Smooth. No stipules present.

FLOWER

Natural flowering season: Spring through Summer.

Days to flowering from rooted cutting: Ten weeks.

Inflorescence and flower type and habit: Fully double, straight on top of peduncle (average angle 0°) to slightly outward (average angle 30°).

Rate of flower opening: 14 to 21 days from bud to fully opened flower.

Flower longevity on plant: Approx. 2 weeks.

Persistent or self-cleaning: Persistent.

Bud:

*Shape.*—Flattened globular.

*Length.*—1.2 cm.

*Diameter.*—1.5 cm.

*Color.*—Near RHS Yellow-Green 151A.

Flower size:

*Diameter.*—Approximately 10.4 cm.

*Depth.*—Approximately 4.9 cm.

Petals:

*Quantity.*—Approx. 120.

*Arrangement.*—Rotate, in 6 rows.

*Length.*—Approximately 4.1 cm.

*Width.*—Approximately 2.5 cm.

*Shape.*—Obovate, base fused.

*Apex.*—Obtuse.

*Base.*—Cuneate.

*Margin.*—Entire.

*Texture, upper and lower surfaces.*—Smooth, slightly velvety.

Color:

*When opening, upper surface.*—Near RHS Red 46A.

*When opening, lower surface.*—Near RHS Orange-Red N34A.

*Fully opened, upper surface.*—Near RHS Red 46B.

*Fully opened, lower surface.*—Near RHS Orange-Red N34A.

Sepals:

*Quantity.*—9.

*Length.*—Approximately 1.6 cm.

*Width.*—Approximately 0.7 cm.

*Shape (overall).*—Ovate to elliptic.

*Apex.*—Bluntly acute.

*Base.*—Cuneate.

*Margin.*—Entire.

*Color.*—Near RHS Green 137B.

Peduncles:

*Length.*—Approximately 8.3 cm.

*Diameter.*—Approximately 0.3 cm.

*Angle.*—About 0° to the lateral branch (=straight on top of lateral branch).

*Strength.*—Strong.

*Texture.*—Smooth, glossy.

*Color.*—Near RHS Yellow-Green 146A.

*Strength.*—Strong.

Fragrance: Very faint.

REPRODUCTIVE ORGANS

Stamens:

*Number.*—A few (average: 5) disc florets in the centre of the inflorescence carries an average of 4 stamen.

Anthers:

*Shape.*—Linear.

*Length.*—Approximately 0.4 cm.

*Color.*—Near RHS Yellow 14A.

*Pollen.*—Color: Near RHS Yellow 17A. Quantity: Low to moderate.

Pistil: No pistil present.

OTHER CHARACTERISTICS

Seeds and fruits: Not observed to date.

Disease/pest resistance: Neither resistance nor susceptibility to pathogens and pests common to *Dahlia* have been observed.

Temperature tolerance: The new variety tolerates temperatures between 10 to 35° C.

What is claimed is:

1. A new and distinct cultivar of *Dahlia* plant named 'LOMDAHBRS' as herein illustrated and described.

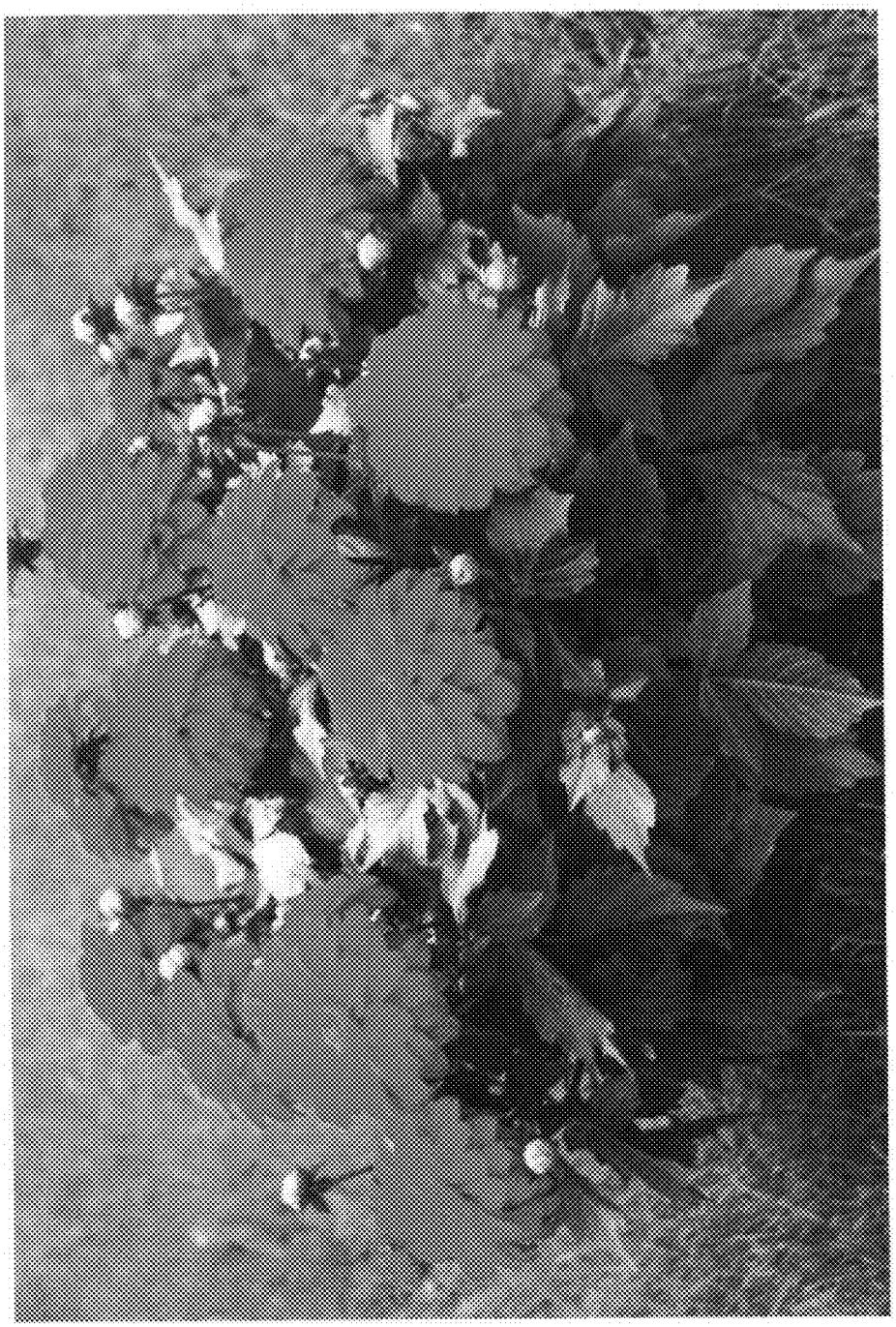

* * * * *